US012660987B2

(12) United States Patent
Morimoto et al.

(10) Patent No.: US 12,660,987 B2
(45) Date of Patent: Jun. 23, 2026

(54) ENDOSCOPE WITH TREATMENT TOOL DELIVERY PORT AND ELEVATOR

(71) Applicant: FUJIFILM Corporation, Tokyo (JP)

(72) Inventors: Yasuhiko Morimoto, Kanagawa (JP); Tsuneo Fukuzawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1312 days.

(21) Appl. No.: 17/179,359

(22) Filed: Feb. 18, 2021

(65) Prior Publication Data

US 2021/0169313 A1      Jun. 10, 2021

Related U.S. Application Data

(63) Continuation of application No. PCT/JP2019/033255, filed on Aug. 26, 2019.

(30) Foreign Application Priority Data

Sep. 10, 2018      (JP) ................................. 2018-169147

(51) Int. Cl.
*A61B 1/00*          (2006.01)
*A61B 1/015*          (2006.01)
          (Continued)

(52) U.S. Cl.
CPC .......... *A61B 1/00091* (2013.01); *A61B 1/018* (2013.01); *A61B 1/06* (2013.01);
          (Continued)

(58) Field of Classification Search
CPC ... A61B 1/00091; A61B 1/0625; A61B 1/018; A61B 1/06; A61B 1/015; A61B 8/12; A61B 8/445; A61B 8/14
See application file for complete search history.

(56) References Cited

U.S. PATENT DOCUMENTS 4,646,722 A * 3/1987 Silverstein ......... A61B 1/00142
                                                                600/122
7,946,993 B2    5/2011 Kohno
                    (Continued)

FOREIGN PATENT DOCUMENTS

CN          104717914          6/2015
CN          108498120          9/2018
                    (Continued)

OTHER PUBLICATIONS

Office Action of China Counterpart Application, with English translation thereof, issued on Oct. 21, 2023, pp. 1-16.
                    (Continued)

*Primary Examiner* — Michael J Carey
*Assistant Examiner* — William B Chou
(74) *Attorney, Agent, or Firm* — JCIPRNET

(57)          ABSTRACT

Provided is an endoscope capable of reliably illuminating a treatment tool delivered from a treatment tool delivery port and a treatment target region thereof.
An endoscope includes a distal end part body that is provided on a distal end side of an insertion part and has a distal end, a proximal end, and a longitudinal axis; the treatment tool delivery port that is formed in the distal end part body and delivers the treatment tool inserted into the insertion part; an elevator that is rotatably supported in the treatment tool delivery port of the distal end part body and controls a delivery direction of the treatment tool delivered from the treatment tool delivery port; and a first illumination window that is provided on the distal end part body. The first illumination window is provided in a proximal end side region at a position shifted from the treatment tool delivery port to a proximal end side of the distal end part body in the distal end part body.

7 Claims, 11 Drawing Sheets

(51) Int. Cl.

| | |
|---|---|
| *A61B 1/018* | (2006.01) |
| *A61B 1/06* | (2006.01) |
| *A61B 8/00* | (2006.01) |
| *A61B 8/12* | (2006.01) |
| *A61B 8/14* | (2006.01) |

(52) U.S. Cl.

CPC .............. *A61B 1/0625* (2022.02); *A61B 8/12* (2013.01); *A61B 8/445* (2013.01); *A61B 1/015* (2013.01); *A61B 8/14* (2013.01)

(56) References Cited

U.S. PATENT DOCUMENTS

| | | | |
|---|---|---|---|
| 11,246,478 B2 | 2/2022 | Morimoto et al. | |
| 2005/0228289 A1 | 10/2005 | Kohno | |
| 2007/0265499 A1* | 11/2007 | Wood ................. | A61B 1/00183 |
| | | | 600/137 |
| 2007/0270638 A1* | 11/2007 | Kitano ............... | A61B 1/00098 |
| | | | 600/114 |
| 2008/0021269 A1* | 1/2008 | Tinkham ............ | A61B 1/00098 |
| | | | 600/104 |
| 2012/0018481 A1 | 1/2012 | Hall et al. | |
| 2012/0184811 A1 | 7/2012 | Chen | |
| 2015/0031947 A1 | 1/2015 | Kudo et al. | |

| | | | |
|---|---|---|---|
| 2018/0185045 A1* | 7/2018 | Ohki ...................... | A61B 1/009 |
| 2018/0235453 A1* | 8/2018 | Morimoto .............. | A61B 1/126 |
| 2018/0242832 A1* | 8/2018 | Morimoto .......... | A61B 1/00177 |

FOREIGN PATENT DOCUMENTS

| | | |
|---|---|---|
| JP | S56158646 | 12/1981 |
| JP | H08126604 | 5/1996 |
| JP | H08126643 | 5/1996 |
| JP | 2005287526 | 10/2005 |
| JP | 2012090741 | 5/2012 |
| JP | 2012148051 | 8/2012 |
| JP | 2014033716 | 2/2014 |
| JP | 2018110741 | 7/2018 |
| WO | 2014136326 | 9/2014 |

OTHER PUBLICATIONS

"International Search Report (Form PCT/ISA/210) of PCT/JP2019/033255," mailed on Nov. 12, 2019, with English translation thereof, pp. 1-5.

"International Preliminary Report on Patentability (Form PCT/IPEA/409) of PCT/JP2019/033255," completed on Jun. 11, 2020, with English translation thereof, pp. 1-25.

"Office Action of Japan Counterpart Application" with English translation thereof, issued on May 13, 2022, p. 1-p. 9.

* cited by examiner

2

43

42

24

38

36

10

22

44

62

64

50

52

54

20

30

32

28

ENDOSCOPE
PROCESSOR
DEVICE

14

LIGHT
SOURCE
DEVICE

16

WATER
SUPPLY
TANK

118

34

27

ULTRASOUND
PROCESSOR
DEVICE

MONITOR

18

SUCTION
PUMP

124

12

ENDOSCOPE WITH TREATMENT TOOL DELIVERY PORT AND ELEVATOR

CROSS-REFERENCE TO RELATED APPLICATIONS

The present application is a Continuation of PCT International Application No. PCT/JP2019/033255 filed on Aug. 26, 2019 claiming priority under 35 U.S.C § 119(a) to Japanese Patent Application No. 2018-169147 filed on Sep. 10, 2018. Each of the above applications is hereby expressly incorporated by reference, in its entirety, into the present application.

BACKGROUND OF THE INVENTION

1. Field of the Invention

The present invention relates to an endoscope including a treatment tool delivery port and an elevator on a distal end side of an insertion part.

2. Description of the Related Art

As an ultrasound endoscope, there is known one in which an electronic scanning type ultrasound transducer is provided at a distal end part of an insertion part of the endoscope and a treatment tool delivery port is disposed on a proximal end side of the ultrasound transducer in the distal end part. In endoscopy using this ultrasound endoscope, for example, while acquiring an ultrasound image of a treatment target region (including an observed region, an examined region, and the like) with the ultrasound transducer, cells are collected by puncturing a treatment target region with a puncturing treatment tool delivered into the body through a treatment tool insertion channel and a treatment tool delivery port. Also, in order to treat a desired position with such a treatment tool, it is necessary to change the delivery direction of the treatment tool delivered from the treatment tool delivery port formed at the distal end part of the insertion part. For this reason, a treatment tool elevating mechanism is provided inside the treatment tool delivery port of the distal end part of the insertion part (refer to JP1996-126643A (H08-126643A), JP1996-126643A (H08-126604A), and JP2005-287526A).

The treatment tool elevating mechanism includes an elevator housing chamber, an elevator, an elevator rotating mechanism, and the like. The elevator housing chamber is provided in the treatment tool delivery port of the distal end part of the insertion part. The elevator is supported in the elevator housing chamber so as to be rotatable about a rotation shaft. The elevator rotating mechanism rotates the elevator depending on the rotational operation of the elevator, which is performed by the operating part of the ultrasound endoscope.

In addition to the already-described treatment tool delivery port, an observation window for observing the treatment target region, and an illumination window for emitting illumination light toward the treatment target region and the like are provided on an outer surface of the distal end part of the insertion part.

For example, in ultrasound endoscopes described in JP1996-126643A (H08-126643A) and JP1996-126643A (H08-126604A), in a case where a direction parallel to the rotation shaft of the elevator is the width direction of the treatment tool delivery port, the observation window and the illumination window are provided at a position on one direction side of the treatment tool delivery port in the width direction at the outer periphery of the distal end part of the insertion part. Additionally, in an ultrasound endoscope described in JP2005-287526A, the observation window and a first illumination window are provided at a position on the one direction side in the width direction with respect to the treatment tool delivery port at the distal end part of the insertion part, and a second illumination window is provided at a position on the other direction side opposite to the one direction side with respect to the treatment tool delivery port.

SUMMARY OF THE INVENTION

In recent years, a therapeutic procedure has been performed in which a stent (corresponding to the treatment tool) is placed in a lumen, for example, the stomach by using an ultrasound endoscope. In a case where the stent is placed in the stomach, it is important for therapeutic safety to optically observe the stent not only by an ultrasound image but also by an endoscope image. For example, in a case where the intrahepatic bile duct and the stomach are connected to each other with a stent in order to relieve the jaundice symptom, it is necessary to confirm in real time that the stent is accurately released in the stomach on the basis of the endoscope image. For this reason, it is necessary to reliably illuminate the treatment tool such as a stent delivered from the treatment tool delivery port and the treatment target region with the illumination light.

In the ultrasound endoscopes described in JP1996-126643A (H08-126643A) and JP1996-126643A (H08-126604A), the treatment tool and the treatment target region are illuminated only by the illumination window disposed on one direction side of the treatment tool delivery port. For this reason, in a case where the treatment target region enters the shadow of the elevator and the treatment tool, there is a concern that the illumination light does not hit the treatment target region. Additionally, since the way the illumination light hits the treatment tool changes due to the displacement of the treatment tool accompanying the rotation of the elevator, there is a concern that the endoscope image is not easily seen and the treatment tool delivered from the treatment tool delivery port and the treatment target region may be out of the illumination range of the illumination light.

Additionally, in the ultrasound endoscope described in JP2005-287526A, the treatment target region is illuminated from two directions by the first illumination window and the second illumination window, and the illumination light amount is also increased as compared to the ultrasound endoscopes described in JP1996-126643A (H08-126643A) and JP1996-126643A (H08-126604A). Therefore, the treatment target region does not easily enter the shadow of the elevator and the treatment tool. However, also in the ultrasound endoscope described in JP2005-287526A, there is a concern that the treatment tool delivered from the treatment tool delivery port and the treatment target region thereof may be out of the illumination range of the illumination light depending on the rotational position of the elevator.

The present invention has been made in view of such circumstances, and an object of the present invention is to provide an endoscope capable of reliably illuminating a treatment tool delivered from a treatment tool delivery port and a treatment target region thereof.

An endoscope for achieving the object of the present invention is an endoscope comprising a distal end part body that is provided on a distal end side of an insertion part and has a distal end, a proximal end, and a longitudinal axis; a treatment tool delivery port that is formed in the distal end part body and delivers a treatment tool inserted into the insertion part; an elevator that is rotatably supported in the treatment tool delivery port of the distal end part body and controls a delivery direction of the treatment tool delivered from the treatment tool delivery port, and a first illumination window that is provided on the distal end part body. The first illumination window is provided in a proximal end side region at a position shifted from the treatment tool delivery port to a proximal end side of the distal end part body in the distal end part body.

According to this endoscope, the treatment tool delivered from the treatment tool delivery port and the treatment target region thereof can always be illuminated from the proximal end side region with the illumination light emitted from the first illumination window. Thus, it is possible to reliably illuminate the treatment tool and the treatment target region thereof with the illumination light from the first illumination window.

In the endoscope according to another aspect of the present invention, in a case where a direction perpendicular to both the longitudinal axis and a normal direction of an opening surface of the treatment tool delivery port is a width direction of the treatment tool delivery port, the proximal end side region is a region in the distal end part body, which is located closer to the proximal end side of the distal end part body than the treatment tool delivery port and is present within a range in which the treatment tool delivery port is formed in the width direction. Accordingly, it is possible to reliably illuminate the treatment tool and the treatment target region thereof with the illumination light from the first illumination window.

The endoscope according to another aspect of the present invention further comprises an elevator support member that is coupled to one end part of the elevator and rotatably supports the elevator between an elevated position and a lodged position. The other end part of the elevator opposite to the one end part is provided at a position closer to a distal end side of the distal end part body than the first illumination window at least in a case where the elevator is at the lodged position. Accordingly, it is possible to reliably illuminate the treatment tool and the treatment target region thereof with the illumination light from the first illumination window.

In the endoscope according to another aspect of the present invention, in a case where a direction perpendicular to both the longitudinal axis and a normal direction of an opening surface of the treatment tool delivery port is a width direction of the treatment tool delivery port, a first illumination axis of the first illumination window is inclined toward a distal end side of the distal end part body from a posture perpendicular to both the width direction and the longitudinal axis, and the proximal end side region is an inclined surface having the first illumination axis as a normal line. Accordingly, it is possible to reliably illuminate the treatment tool and the treatment target region thereof with the illumination light from the first illumination window.

The endoscope according to still another aspect of the present invention further comprises an observation window that is provided at a position closer to the proximal end side of the distal end part body than the treatment tool delivery port in the distal end part body, and a first illumination range of illumination light emitted from the first illumination window includes an observation range of the observation window. Accordingly, the visibility of the observation range of the observation window can be improved.

In the endoscope according to still another aspect of the present invention, in a case where a direction perpendicular to both the longitudinal axis and a normal direction of an opening surface of the treatment tool delivery port is a width direction of the treatment tool delivery port, the observation window is provided at a position on one direction side in the width direction with respect to the proximal end side region in the distal end part body. By disposing the observation window and the first illumination window at substantially the same position in the direction along the longitudinal axis, the observation range of the observation window can be illuminated with the illumination light emitted from the first illumination window.

The endoscope according to still another aspect of the present invention further comprises a second illumination window provided at a position on the other direction side opposite to the one direction side with respect to the proximal end side region in the distal end part body, and the second illumination window illuminates a second illumination range that partially overlaps the first illumination range and includes the observation range. Accordingly, the observation range of the observation window can be illuminated with the illumination light emitted from both the first illumination window and the second illumination window.

In the endoscope according to still another aspect of the present invention, both a first illumination axis of the first illumination window and a second illumination axis of the second illumination window are inclined toward the distal end side of a distal end part body from a posture perpendicular to both the width direction and the longitudinal axis, and a second illumination axis angle is smaller than a first illumination axis angle in a case where an inclination angle of the first illumination axis with respect to a reference axis parallel to the longitudinal axis as seen from the width direction side is the first illumination axis angle and an inclination angle of the second illumination axis with respect to the reference axis as seen from the width direction side is the second illumination axis angle. Accordingly, the visibility (forward visibility) of the insertion part 20 on the insertion direction side can be improved.

In the endoscope according to still another aspect of the present invention, an observation axis of the observation window is inclined toward the distal end side of the distal end part body from the posture perpendicular to both the width direction and the longitudinal axis, and an observation axis angle is equal to the first illumination axis angle in a case where an inclination angle of the observation axis with respect to the reference axis as seen from the width direction side is the observation axis angle. Accordingly, the observation range of the observation window can be included in the first illumination range of the first illumination window.

The endoscope according to still another aspect of the present invention further comprises an ultrasound transducer that is provided in the distal end part body and is located closer to a distal end side of the distal end part body than the treatment tool delivery port.

The present invention can reliably illuminate the treatment tool delivered from the treatment tool delivery port and the treatment target region thereof.

DESCRIPTION OF THE PREFERRED EMBODIMENTS

[Configuration of Ultrasound Examination System and Ultrasound Endoscope]

Figure 1:
FIG. 1 is a schematic view of an ultrasound examination system to which an endoscope of the present invention is applied.

FIG. 1 is a schematic view of an ultrasound examination system 2 to which an endoscope of the present invention is applied. As illustrated in FIG. 1, the ultrasound examination system 2 includes an ultrasound endoscope 10 that images the inside of a lumen 154 (also referred to as a body cavity, refer to FIG. 12) of a subject, an ultrasound processor device 12 that generates an ultrasound image, an endoscope processor device 14 that generates an endoscope image, a light source device 16 that supplies illumination light for illuminating the inside of the lumen 154 to the ultrasound endoscope 10, and a monitor 18 for displaying the ultrasound image and the endoscope image.

The ultrasound endoscope 10 corresponds to the endoscope of the present invention and includes an insertion part 20, an operating part 22, and a universal cord 24.

Figure 12:
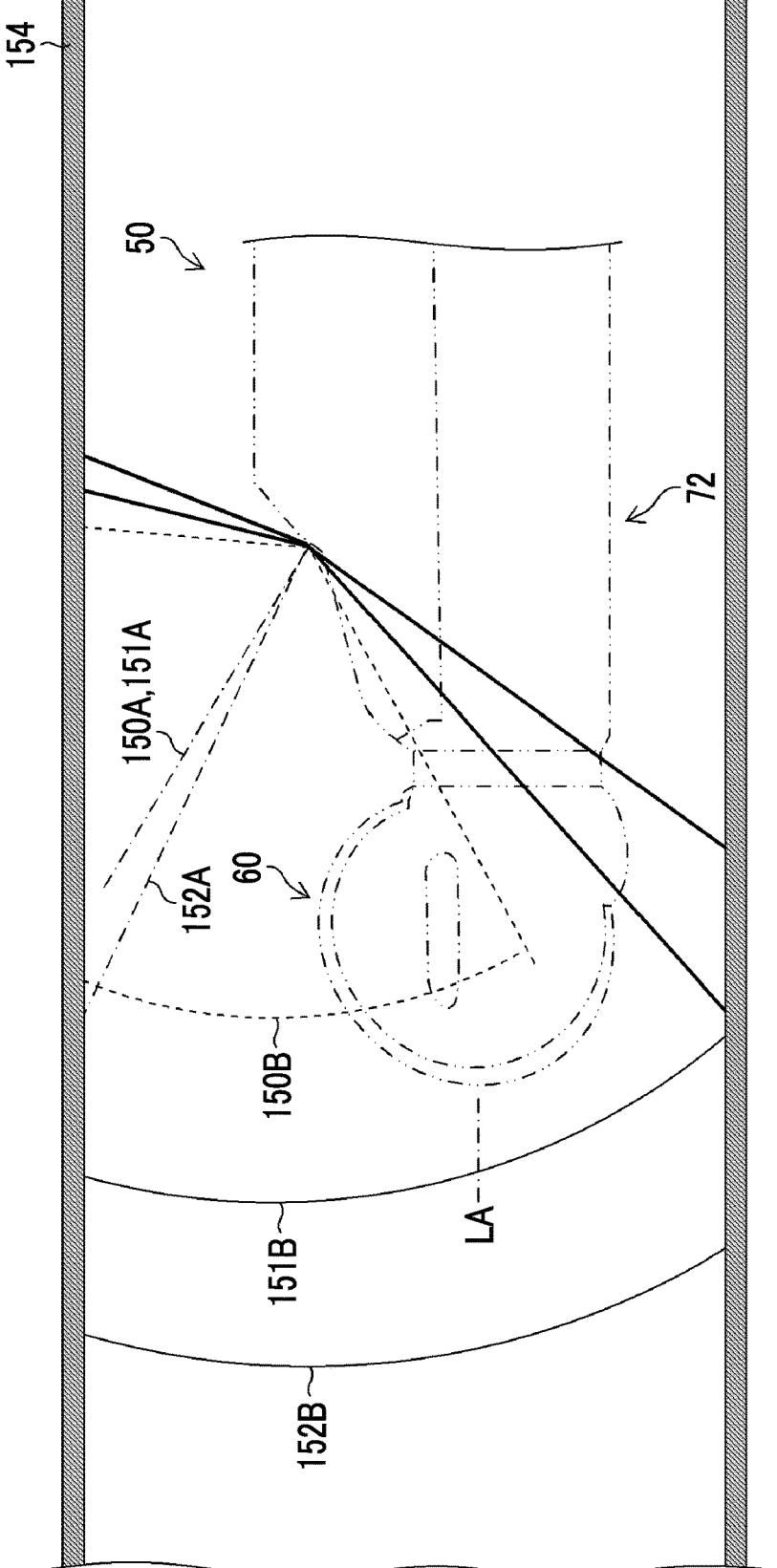
FIG. 12 is a side view of the distal end part of the insertion part inserted into a lumen.

The insertion part 20 is inserted into various lumens 154 (refer to FIG. 12). The operating part 22 is continuously provided on a proximal end side of the insertion part 20 and receives an operation of a surgeon.

The operating part 22 is connected to one end side of the universal cord 24. Additionally, an ultrasound connector 27 connected to the ultrasound processor device 12, an endoscope connector 28 connected to the endoscope processor device 14, and a light source connector 30 connected to the light source device 16 are provided on the other end side of the universal cord 24. A water supply tank 118 is connected to the light source connector 30 via an air and water supply tube 32, and a suction pump 124 is connected to light source connector 30 via a suction tube 34.

The ultrasound processor device 12 generates an ultrasound image on the basis of an ultrasound detection signal output from the ultrasound endoscope 10. Additionally, the endoscope processor device 14 also generates an endoscope image on the basis of an imaging signal output from the ultrasound endoscope 10.

The light source device 16 is connected to the insertion part 20, the operating part 22, the universal cord 24, and an incident end of a light guide 128 (refer to FIG. 2) inserted into the light source connector 30. The light source device 16 supplies illumination light to the incident end of the light guide 128. The illumination light is emitted from the light guide 128 to treatment target regions through respective illumination windows 90A and 90B (refer to FIG. 3) described below.

The monitor 18 is connected to both the ultrasound processor device 12 and the endoscope processor device 14 and displays an ultrasound image generated by the ultrasound processor device 12 and the endoscope image generated by the endoscope processor device 14. With regard to the display of the ultrasound image and the endoscope image, only any one of the images can be selectively displayed or both of the images can be simultaneously displayed.

An air and water supply button 36 and a suction button 38 and are provided side by side on the operating part 22, which is provided with a pair of angle knobs 42, an operating lever 43, a treatment tool insertion port 44, and the like.

The insertion part 20 has a distal end, a proximal end, and a longitudinal axis and has a distal end part 50, a bending part 52, and a flexible part 54 in order toward the proximal end side from the distal end side. The distal end part 50 is formed of a hard member and is also referred to as a distal end hard part. An ultrasound transducer 62 is provided on the distal end part 50 on which a balloon 64 that covers the ultrasound transducer 62 is attachably and detachably mounted.

The bending part 52 has one end continuously provided on the proximal end side of the distal end part 50 and the other end continuously provided on the distal end side of the flexible part 54. The bending part 52 is configured to be bendable and is operated to be remotely bent by performing the rotational movement operation of the pair of angle knobs 42. Accordingly, the distal end part 50 can be oriented in a desired direction.

The flexible part 54 has a small diameter, a long length, and flexibility and couples the bending part 52 to the operating part 22.

Figure 2:
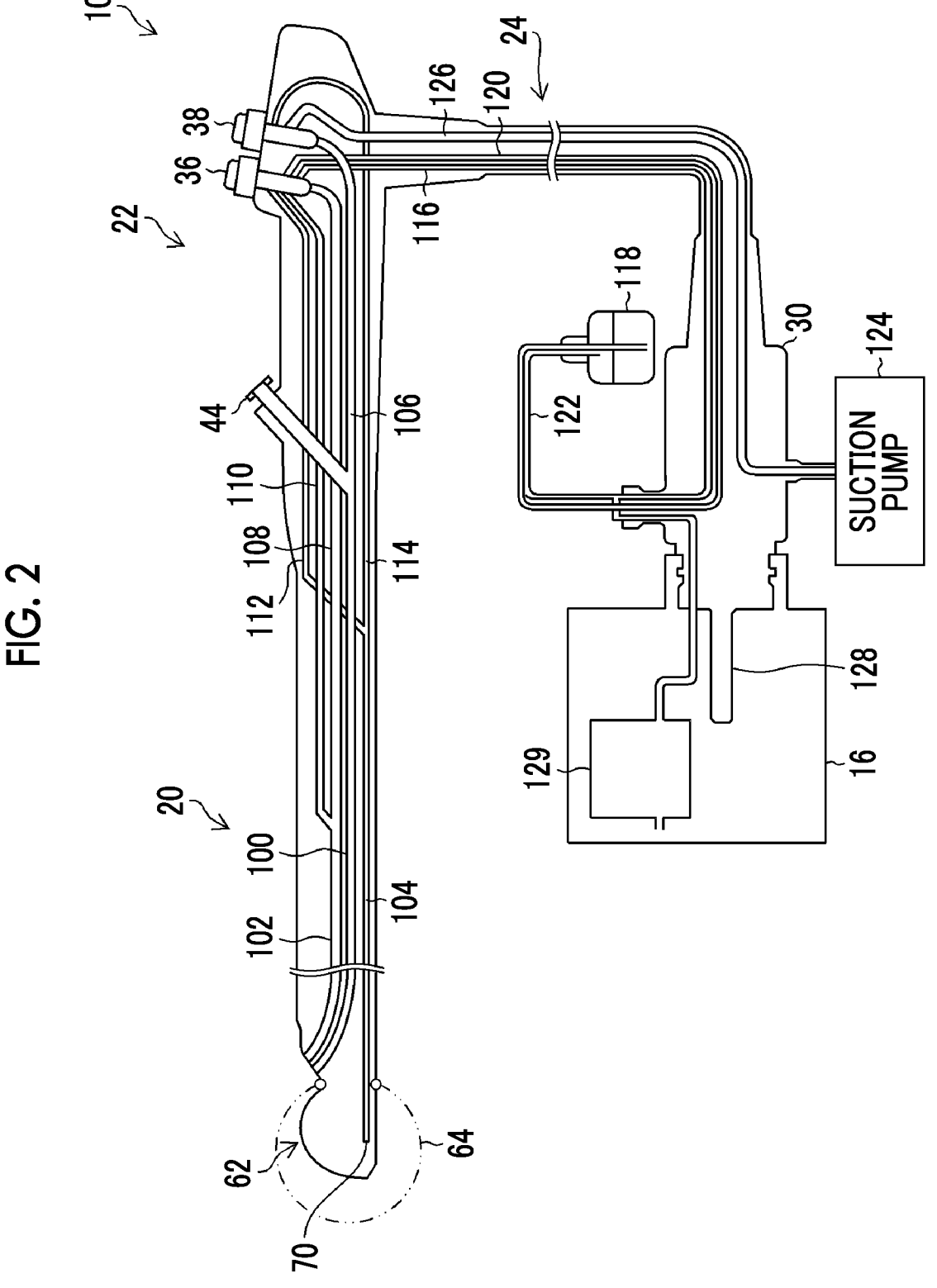
FIG. 2 is a schematic view illustrating a pipe line configuration of an ultrasound endoscope.

FIG. 2 is a schematic view illustrating a pipe line configuration of the ultrasound endoscope 10. As illustrated in FIG. 2, a treatment tool insertion channel 100, an air and water supply pipe line 102, and a balloon pipe line 104 having one end leading to an internal space of the balloon 64 are provided inside the insertion part 20 and the operating part 22.

One end side of the treatment tool insertion channel 100 is connected to an elevating case 200 (refer to FIG. 3) described below, and the other end side of the treatment tool insertion channel 100 is connected to the treatment tool insertion port 44 in the operating part 22. Accordingly, the treatment tool insertion port 44 and the treatment tool delivery port 94 (refer to FIG. 3) described below communicate with each other via the treatment tool insertion channel 100. Additionally, a suction pipe line 106 is branched from the treatment tool insertion channel 100, and the suction pipe line 106 is connected to the suction button 38.

One end side of the air and water supply pipe line 102 is connected to an air and water supply nozzle 92 (refer to FIG. 3) described below, and the other end side of the air and water supply pipe line 102 is branched into an air supply pipe line 108 and a water supply pipe line 110. The air supply pipe line 108 and the water supply pipe line 110 are connected to the air and water supply button 36, respectively.

One end side of the balloon pipe line 104 is connected to a supply and discharge port 70 that opens at a position inside the balloon 64 in an outer peripheral surface of the distal end part 50, and the other end side of the balloon pipe line 104 is branched to a balloon water supply pipeline 112 and a balloon drainage pipeline 114. The balloon water supply pipeline 112 is connected to the air and water supply button 36, and the balloon drainage pipe line 114 is connected to the suction button 38.

In addition to the air supply pipe line 108, the water supply pipe line 110, and the balloon water supply pipe line 112, one end side of an air supply source pipe line 116 leading to an air supply pump 129 and one end side of a water supply source pipe line 120 leading to the water supply tank 118 are connected to the air and water supply button 36. The air supply pump 129 always operates during ultrasound observation.

A branch pipe line 122 is branched from the air supply source pipe line 116, and the branch pipe line 122 is connected to an inlet (above a liquid surface) of the water supply tank 118. Additionally, the other end side of the water supply source pipe line 120 is inserted into the water supply tank 118 (below the liquid surface). Then, in a case where the internal pressure of the water supply tank 118 rises due to the air supply from the air supply pump 129 via the branch pipe line 122, the water in the water supply tank 118 is supplied to the water supply source pipe line 120.

As the air and water supply button 36, a publicly known two-stage switchable button is used. The air and water supply button 36 switches between the leak of air sent from the air supply source pipe line 116, the jetting of air from the air and water supply nozzle 92, the jetting of water supply from the air and water supply nozzle 92, and the supply of water into the balloon 64, depending on the surgeon's operation. In addition, since a specific switching method is a known technique, the description thereof will be omitted here.

In addition to the suction pipe line 106 and the balloon drainage pipe line 114, one end side of a suction source pipe line 126 is connected to the suction button 38. A suction pump 124 is connected to the other end side of the suction source pipe line 126. The suction pump 124 also always operates during the ultrasound observation. The suction button 38 is a two-stage switchable button similar to the air and water supply button 36.

The suction button 38 switches between the communication of the suction source pipe line 126 with the outside (atmosphere), the suction of various suctioned materials from the treatment tool delivery port 94 (refer to FIG. 3), and the drainage of water in the balloon 64, depending on the surgeon's operation. In addition, since a specific switching method is a known technique, the description thereof will be omitted here.

Returning to FIG. 1, although the operating lever 43 of the operating part 22 is described in detail below, the operating lever 43 is used for the operation of changing the delivery direction of a treatment tool (not illustrated, the same applies below) delivered from the treatment tool delivery port 94 (refer to FIG. 3).

[Configuration of Distal End Part of Insertion Part]

Figure 3:
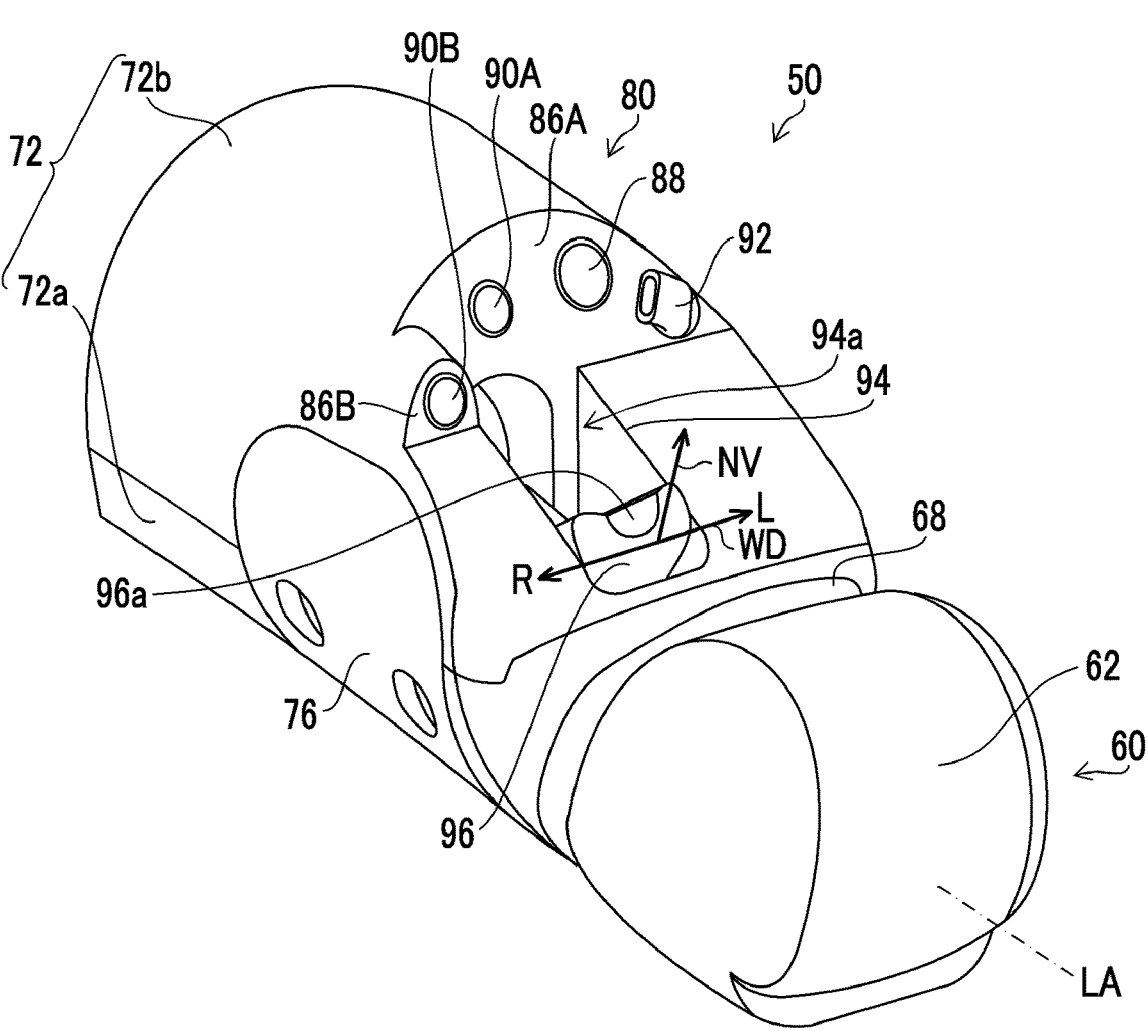
FIG. 3 is an external perspective view of a distal end part of an insertion part.
Figure 4:
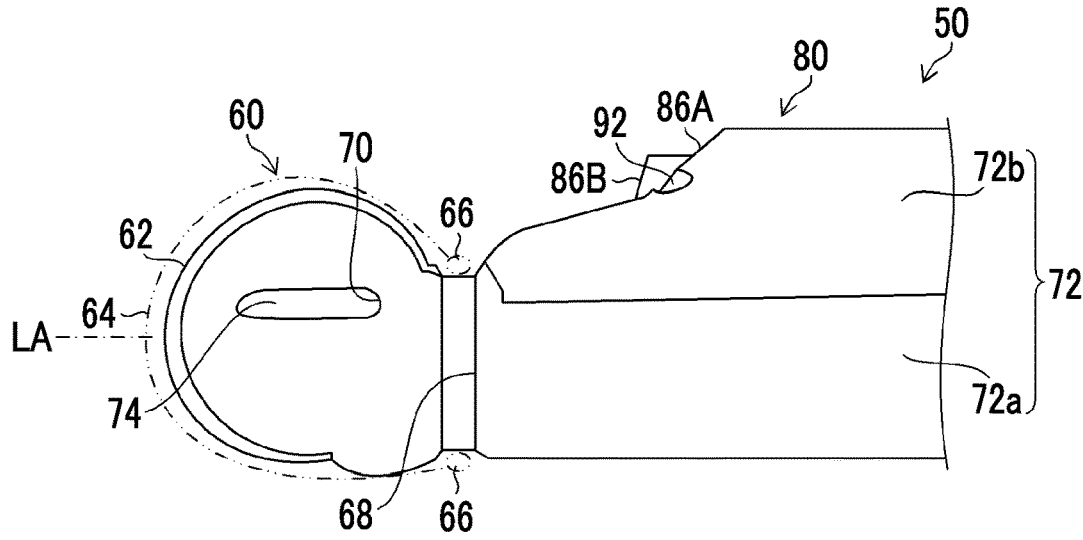
FIG. 4 is a right side view of the distal end part of the insertion part.
Figure 5:
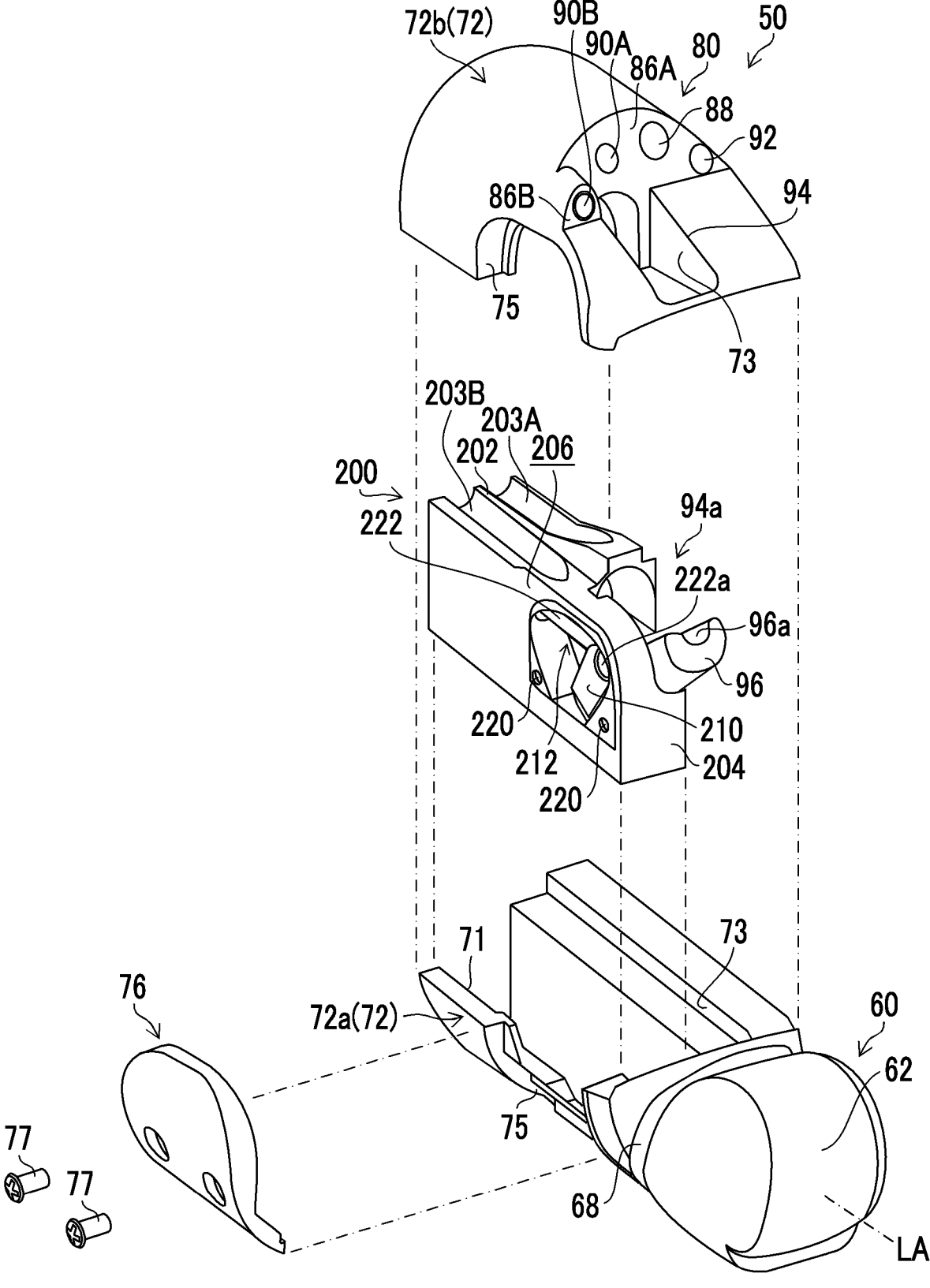
FIG. 5 is an exploded perspective view of the distal end part of the insertion part.

FIG. 3 is an external perspective view of the distal end part 50 of the insertion part 20. FIG. 4 is a right side view of the distal end part 50 of the insertion part 20. FIG. 5 is an exploded perspective view of the distal end part 50 of the insertion part 20. In addition, illustration of the balloon 64 is omitted in FIGS. 3 and 5. Additionally, in FIG. 5, illustration of the light guide 128 is omitted.

As illustrated in FIGS. 3 to 5, the distal end part 50 includes an exterior case 72 (also referred to as a housing) corresponding to a distal end part body of the present invention. The exterior case 72 has a distal end that constitutes the distal end of the insertion part 20, a proximal end that is connected to the bending part 52, and a longitudinal axis LA. Hereinafter, a distal end side of the exterior case 72 is referred to as an "exterior case distal end side", and a proximal end side of the exterior case 72 is referred to as an "exterior case proximal end side".

An ultrasound observation part 60 that acquires an ultrasound detection signal, a treatment tool delivery port 94 for treatment tools, a first inclined surface 86A and a second inclined surface 86B, and an endoscope observation part 80 that acquires an imaging signal are provided from the exterior case distal end side toward the exterior case proximal end side in the exterior case 72. Additionally, an elevator housing chamber 94a and an elevator 96 located inside the treatment tool delivery port 94, and a metallic elevating case 200 (also referred to as an elevator assembly) that rotatably supports the elevator 96 are provided inside the exterior case 72. Moreover, the exterior case 72 includes a lever housing lid 76.

The treatment tool delivery port 94 opens on an outer surface of the exterior case 72 and at a position between the ultrasound observation part 60 and the endoscope observation part 80 (first inclined surface 86A). The treatment tool inserted into the treatment tool insertion channel 100 of the insertion part 20 is delivered from the treatment tool delivery port 94. Hereinafter, as illustrated in FIG. 3, a direction perpendicular to both the longitudinal axis LA and a normal direction NV of an opening surface of the treatment tool delivery port 94 is defined as a width direction WD of the treatment tool delivery port 94, and one direction side in the width direction WD is defined as an L direction side, and the other direction side opposite to the one direction side in the width direction WD is defined as an R direction side.

The first inclined surface 86A and the second inclined surface 86B are inclined surfaces that are inclined toward the exterior case proximal end side from a posture that is parallel to the width direction WD and perpendicular to the longitudinal axis LA. In addition, although described in detail below, the inclination angle of the first inclined surface 86A and the inclination angle of the second inclined surface 86B are different from each other.

On the outer surface of the exterior case 72, the first inclined surface 86A is formed at a position closer to the exterior case proximal end side than the treatment tool delivery port 94 in a direction along the longitudinal axis LA and is formed from a formation region for the treatment tool delivery port 94 to a region on the L direction side in the width direction WD. An observation window 88, a first illumination window 90A, and an air and water supply nozzle 92 of the endoscope observation part 80 are provided on the first inclined surface 86A. In addition, the first inclined surface 86A may be divided into a region where the observation window 88 is provided, a region where the first illumination window 90A is provided, and a region where the air and water supply nozzle 92 is provided.

On the outer surface of the exterior case 72, the second inclined surface 86B is formed closer to the exterior case distal end side than the first inclined surface 86A in the direction along the longitudinal axis LA and formed in a region closer to the R direction side than the formation region for the treatment tool delivery port 94 in the width direction WD. A second illumination window 90B is provided on the second inclined surface 86B. In addition, the second inclined surface 86B may be formed, in the direction along the longitudinal axis LA, at the same position as the first inclined surface 86A or at a position closer to the exterior case proximal end side than the first inclined surface 86A.

The ultrasound observation part 60 is provided at a position closer to the exterior case distal end side than the treatment tool delivery port 94 in the exterior case 72. The ultrasound observation part 60 includes an ultrasound transducer 62 constituted of a plurality of ultrasound vibration elements. Each ultrasound vibration element of the ultrasound transducer 62 are sequentially driven on the basis of a drive signal input from the ultrasound processor device 12. Accordingly, each ultrasound vibration element sequentially generates an ultrasound toward a treatment target region and receives an ultrasound echo (echo signal) reflected by the treatment target region. Then, each ultrasound vibration element outputs an ultrasound detection signal (electrical signal) according to the received ultrasound echo to the ultrasound processor device 12 via a signal cable (not illustrated) inserted into the insertion part 20, the universal cord 24, and the like. As a result, an ultrasound image is generated in the ultrasound processor device 12.

The balloon 64 is attached to the exterior case distal end side with respect to the treatment tool delivery port 94 on the exterior case 72, is formed in a bag shape that covers the ultrasound transducer 62, and prevents attenuation of an ultrasound and an ultrasound echo. The balloon 64 is formed of, for example, a stretchable elastic material such as latex rubber, and a stretchable locking ring 66 is provided at an opening end on the exterior case proximal end side. A locking groove 68 is provided between the ultrasound observation part 60 and the treatment tool delivery port 94 over the entire circumference in the circumferential direction of the exterior case 72 in the exterior case 72. Then, by fitting the locking ring 66 into the locking groove 68, the balloon 64 is attachably and detachably mounted on the exterior case 72.

The endoscope observation part 80 has the observation window 88 provided on the first inclined surface 86A. Although not illustrated, an observation optical system (objective lens or the like), and a charge coupled device (CCD) type or complementary metal oxide semiconductor (CMOS) type imaging element, and the like, which constitute the endoscope observation part 80, are disposed in the exterior case 72 and behind the observation window 88. The imaging element captures an observation image taken from the observation window 88. Then, the imaging element outputs an imaging signal of the observation image to the endoscope processor device 14 via the signal cable (not illustrated) inserted into the insertion part 20, the universal cord 24, and the like. As a result, the endoscope processor device 14 generates an endoscope image.

The first illumination window 90A and the second illumination window 90B emit illumination light toward the front thereof, which will be described in detail below. Emitting ends of the already-described respective light guides 128 are disposed in the exterior case 72 and behind the respective illumination windows 90A and 90B. Therefore, by coupling the light source connector 30 to the light source device 16 as illustrated in the already-described FIG. 2, the illumination light emitted from the light source device 16 is guided to each of the illumination windows 90A and 90B via the light guide 128, and the illumination light is emitted from each of the illumination windows 90A and 90B.

The air and water supply nozzle 92 is provided at a position in the vicinity of the observation window 88 on the first inclined surface 86A. The air and water supply nozzle 92 is connected to one end side of the air and water supply pipe line 102 illustrated in the already-described FIG. 2 and jets a fluid such as water or air toward the observation window 88 in order to clean foreign matters and the like adhering to the surface of the observation window 88.

The exterior case 72 houses the respective parts of the already-described ultrasound observation part 60 and the endoscope observation part 80, and the elevator 96 and the elevating case 200, which will be described below. A portion of the exterior case 72 closer to the exterior case proximal end side than the ultrasound observation part 60 is divided into two parts in an upward-downward direction in the figure with a plane parallel to both the longitudinal axis LA and the width direction WD as a boundary. For this reason, the exterior case 72 is constituted of the exterior case body 72a located on a lower side in the figure and an exterior case lid 72b located on an upper side in the figure.

The exterior case body 72a houses the ultrasound observation part 60 and has the locking groove 68, at a distal end portion closer to the exterior case distal end side than the treatment tool delivery port 94. Additionally, the exterior case body 72a has an opening part 71 that is provided at a portion closer to the exterior case proximal end side than the locking groove 68 and is covered with the exterior case lid 72b (refer to FIG. 5). Also, the exterior case body 72a houses a portion of each of the elevator 96 and the elevating case 200 in the opening part 71.

A groove part 74 (refer to FIG. 4) formed along the longitudinal axis LA and a supply and discharge port 70 opening at an end part of the groove part 74 on the case proximal end side are formed on a side surface of the distal end portion of the exterior case body 72a on the L direction side. Accordingly, water can be supplied to the inside of the balloon 64 through the supply and discharge port 70, or the water inside the balloon 64 can be discharged.

The exterior case lid 72b is attachably and detachably attached to the opening part 71 of the exterior case body 72a. The exterior case lid 72b is formed with the already-described treatment tool delivery port 94, first inclined surface 86A, and second inclined surface 86B from the exterior case distal end side toward the exterior case proximal end side. Additionally, the exterior case lid 72b covers the endoscope observation part 80 and the two light guides 128 that guide illumination light to the respective illumination windows 90A and 90B.

In a case where the exterior case lid 72b is attached to the opening part 71 of the exterior case body 72a, the elevator housing chamber 94a that is a housing space for the elevator 96 is formed inside the treatment tool delivery port 94. Additionally, the exterior case body 72a and the exterior case lid 72b are formed with a partition wall 73 (refer to FIG. 5) that forms a side surface on the L direction side of the elevator housing chamber 94a so as to straddle both.

A fitting hole 75 (refer to FIG. 5) into which the lever housing lid 76 is fitted is formed so as to straddle the exterior case body 72a and the exterior case lid 72b at the position of the elevating case 200 facing a lever housing chamber 212 to be described below (refer to FIG. 5) on the side surfaces of the exterior case body 72a and the exterior case lid 72b on the R direction side.

The elevator housing chamber 94a communicates with the treatment tool insertion port 44 via the already-described treatment tool insertion channel 100 (refer to FIG. 2). For this reason, the treatment tool inserted into the treatment tool insertion port 44 is introduced into the lumen 154 (refer to FIG. 12) from the treatment tool delivery port 94 via the treatment tool insertion channel 100, the elevator housing chamber 94a, and the like.

The elevator 96 is rotatably supported (pivotally supported) on the elevating case 200 via a rotation shaft 216 (refer to FIG. 6) in the elevator housing chamber 94a. The elevator 96 has an arcuate guide surface 96a that guides a treatment tool guided into the elevator housing chamber 94a toward the treatment tool delivery port 94. Accordingly, the elevator 96 changes the direction of the treatment tool guided into the elevator housing chamber 94a from the treatment tool insertion channel 100 and delivers the treatment tool from the treatment tool delivery port 94. Also, although described in detail below, the elevator 96 rotates about a rotation shaft 216 in the elevator housing chamber 94a depending on the operation of the operating lever 43 and thereby changes the delivery direction of a treatment tool introduced into the lumen 154 (refer to FIG. 12) from the treatment tool delivery port 94. Therefore, the elevator 96 controls the delivery direction of the treatment tool from the treatment tool delivery port 94.

The lever housing lid 76 is fitted into the fitting hole 75 on the outer surface of the exterior case 72. The lever housing lid 76 is attachably and detachably attached to the elevating case 200 by a bolt 77 penetrating the lever housing lid 76 in a state where the lever housing lid 76 is fitted in the fitting hole 75 (refer to FIG. 5).

[Configuration of Elevating Case]

Figure 6:
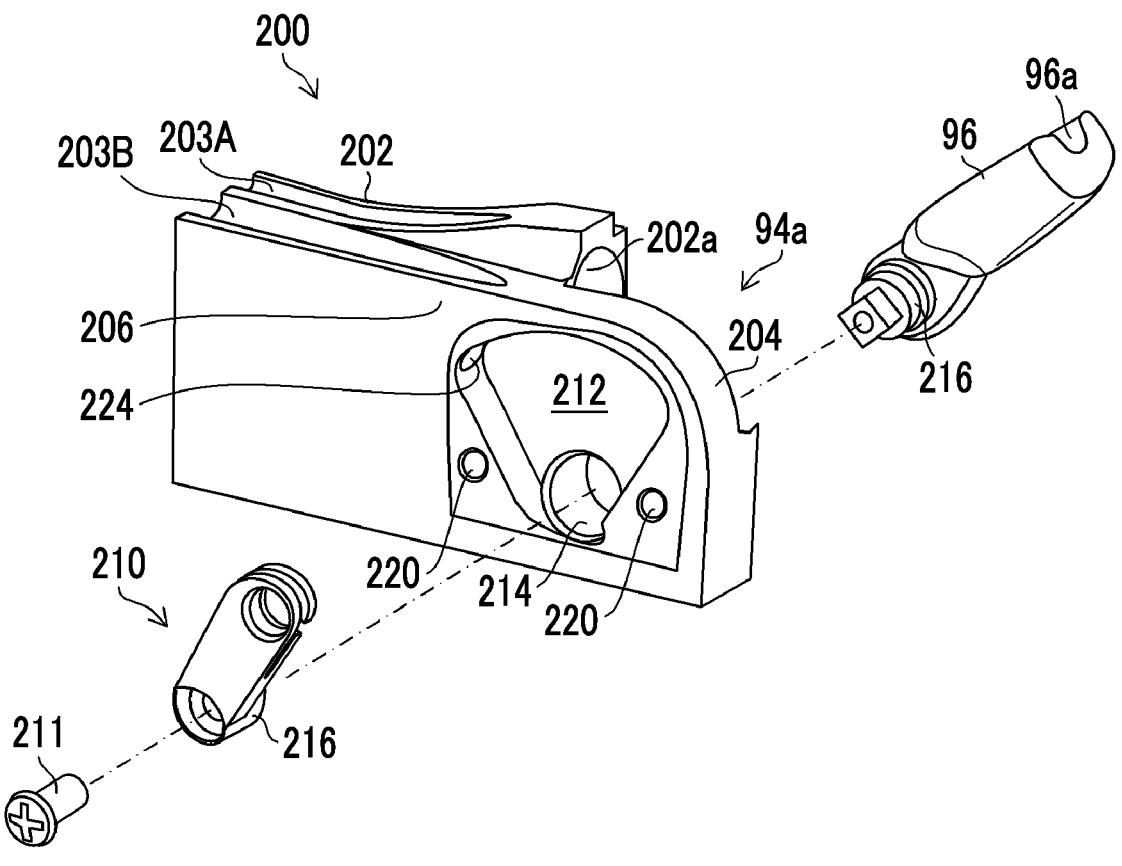
FIG. 6 is a perspective view of an elevating case.
Figure 7:
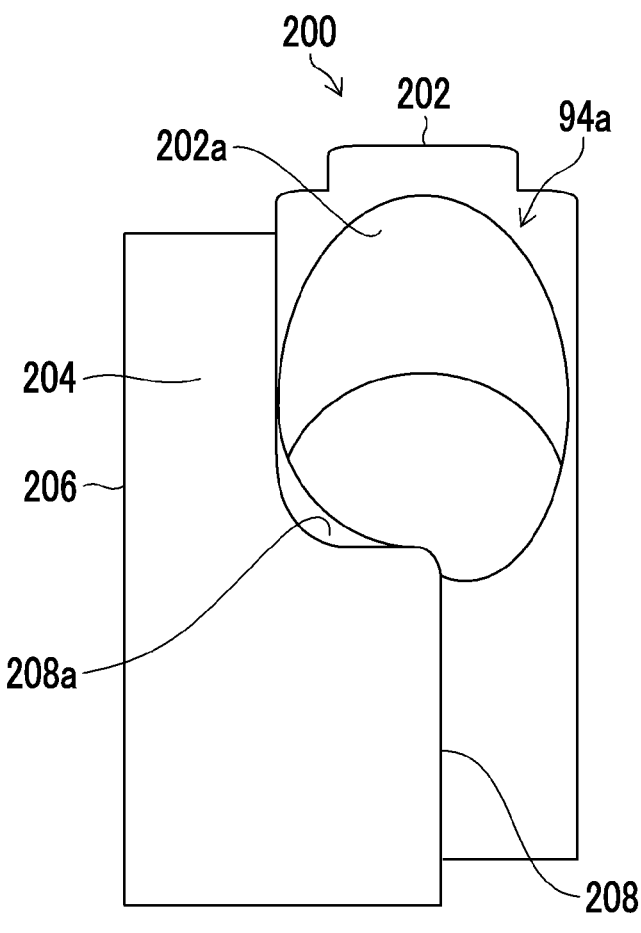
FIG. 7 is a front view of the elevating case in a case where the elevating case is viewed from an exterior case distal end side.

FIG. 6 is a perspective view of the elevating case 200, and FIG. 7 is a front view of the elevating case 200 in a case where the elevating case 200 is viewed from the exterior case distal end side. As illustrated in FIGS. 6 and 7 and the already-described FIG. 5, the elevating case 200 corresponds to an elevator support member of the present invention and is formed of, for example, a metal material having corrosion resistance. The elevating case 200 has a base 202 and a partition wall 204 extending from the base 202 to the exterior case distal end side.

A distal end surface of the base 202 on the exterior case distal end side constitutes a side surface of the elevator housing chamber 94a on the exterior case proximal end side. Additionally, the base 202 is formed with a through hole 202a that is parallel to the longitudinal axis LA and communicates with the elevator housing chamber 94a and the treatment tool insertion channel 100. Accordingly, the treatment tool insertion channel 100 and the elevator housing chamber 94a communicate with each other via the through hole 202a.

Two light guide holding grooves 203A and 203B are formed on an upper surface (a surface on the delivery direction side of the treatment tool) of outer wall surfaces of the base 202. Here, since the illumination windows 90A and 90B are disposed on an upward side (a side perpendicular to both the longitudinal axis LA and the width direction WD) of the elevating case 200, the two light guides 128 corresponding to the illumination windows 90A and 90B, respectively, are disposed along an upper surface of the base 202. Accordingly, each of the light guide holding grooves 203A and 203B allows one emitting end of each light guide 128 to be held at a position facing the first illumination window 90A and allows the emitting end of each light guide 128 to be held at a position facing the second illumination window 90B.

The partition wall 204 is provided between the elevator 96 (elevator housing chamber 94a) and an elevator elevating lever 210 (lever housing chamber 212) described below. The partition wall 204 has a side wall surface 206 that is a side surface on the R direction side, and a facing wall surface 208 that is a side surface on the L direction side and faces the elevator 96.

The lever housing chamber 212 that houses the elevator elevating lever 210 is formed on the side wall surface 206. A holding hole 214 (refer to FIG. 6), which penetrates the partition wall 204 in the width direction WD (an axis direction of the rotation shaft 216), is formed in a bottom surface of the lever housing chamber 212 on the elevator 96 side. The holding hole 214 allows the lever housing chamber 212 and the elevator housing chamber 94a to communicate with each other. Also, the holding hole 214 rotatably and pivotably supports the rotation shaft 216. In addition, since the elevator elevating lever 210 in the lever housing chamber 212 rotates (rocks) about the rotation shaft 216, the lever housing chamber 212 is formed in a fan shape about the rotation shaft 216.

A wire insertion hole 224 (refer to FIG. 6) through which an operating wire 222 is inserted is formed on the side wall surface of the lever housing chamber 212 on the exterior case proximal end side.

A bolt hole 220 into which the already-described bolt 77 is screwed is formed in a peripheral region of the lever housing chamber 212 and a region covered with the lever housing lid 76, in the side wall surface 206. In addition, the numbers of bolts 77 and bolt holes 220 are not particularly limited.

The facing wall surface 208 constitutes a side surface of the elevator housing chamber 94a on the R direction side. A holding hole 214 opens in the facing wall surface 208. Additionally, the facing wall surface 208 is formed with a cutout part 208a (refer to FIG. 7) into which a portion of the elevator 96 is inserted.

The elevator elevating lever 210 rotates the elevator 96 about the rotation shaft 216 depending on the operation of the operating lever 43. One end part of the elevator elevating lever 210 is provided with one of the rotation shafts 216 having a two-split structure, and the operating wire 222 is coupled to the other end part of the elevator elevating lever 210.

One of the rotation shaft 216 having a two-split structure is provided at one end part of the elevator elevating lever 210 as already described, and the other thereof is provided at one end part of the elevator 96. Also, the elevator elevating lever 210 and the elevator 96 are coupled to each other via the rotation shafts 216 having a two-split structure. For example, in the present embodiment, by using the bolt 211 penetrating one end side of the elevator elevating lever 210 to couple one and the other side of the rotation shafts 216 having a two-split structure, the elevator elevating lever 210 and the elevator 96 are coupled to each other via the rotation shaft 216 (refer to FIG. 6). Accordingly, the elevator elevating lever 210 rotates (rocks) integrally with the elevator 96 about the rotation shaft 216.

The operating wire 222 has a distal end side coupling part 222a (refer to FIG. 5) that is coupled to the elevator elevating lever 210 inside the lever housing chamber 212, at one end side thereof. Additionally, the other end side of the operating wire 222 is coupled to an elevator operating mechanism 226 (refer to FIG. 8) in the operating part 22 through the insertion part 20 from a wire insertion hole 224 of the lever housing chamber 212.

Figure 8:
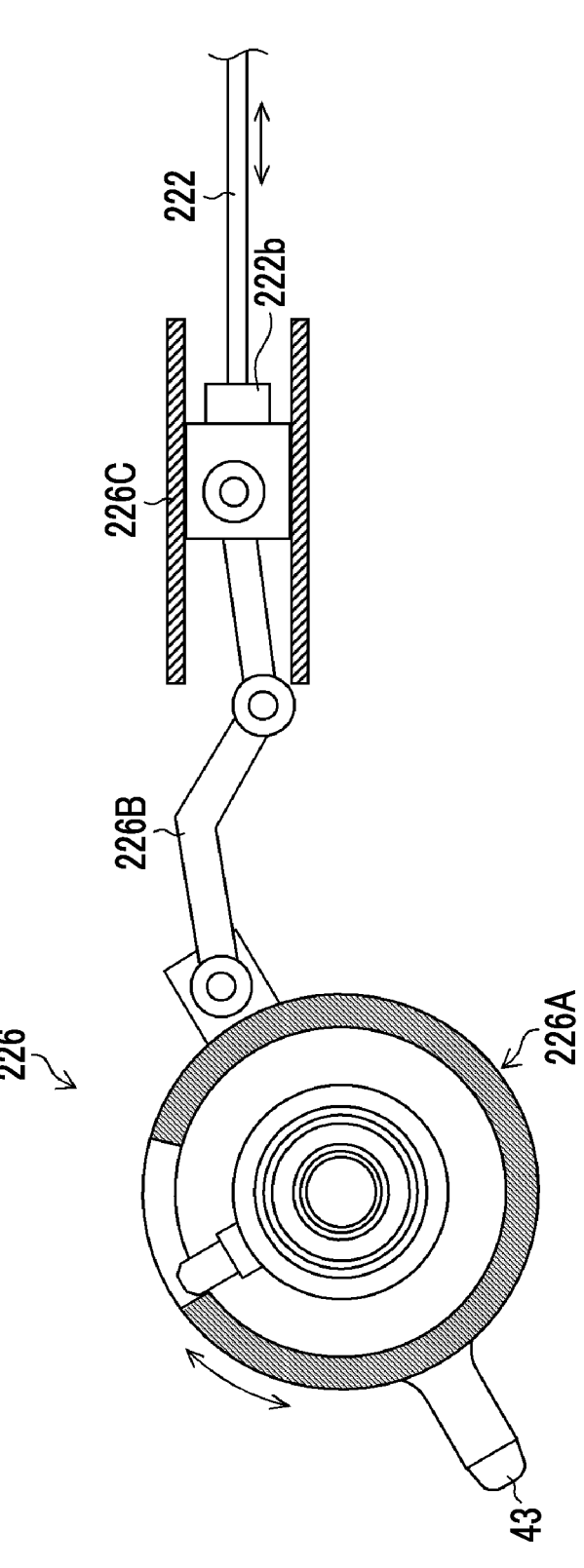
FIG. 8 is a schematic view illustrating an example of an elevator operating mechanism.

FIG. 8 is a schematic view illustrating an example of the elevator operating mechanism 226. As illustrated in FIG. 8, the operating wire 222 has a proximal end side coupling part 222b coupled to the elevator operating mechanism 226, on the proximal end side thereof. The elevator operating mechanism 226 includes the operating lever 43, a rotating drum 226A that is coupled to the operating lever 43 and is rotatable within a certain angle range, a crank member 226B coupled to the rotating drum 226A, and a slider 226C coupled to the crank member 226B. The proximal end side coupling part 222b is coupled to the slider 226C.

In a case where the operating lever 43 is operated to rotate the rotating drum 226A, the operating wire 222 is pushed and pulled via the crank member 226B and the slider 226C, whereby the elevator elevating lever 210 rocks, and the elevator 96 rotates (rocks) about the rotation shaft 216 depending on the rocking of the elevating lever 210.

Figure 9A:
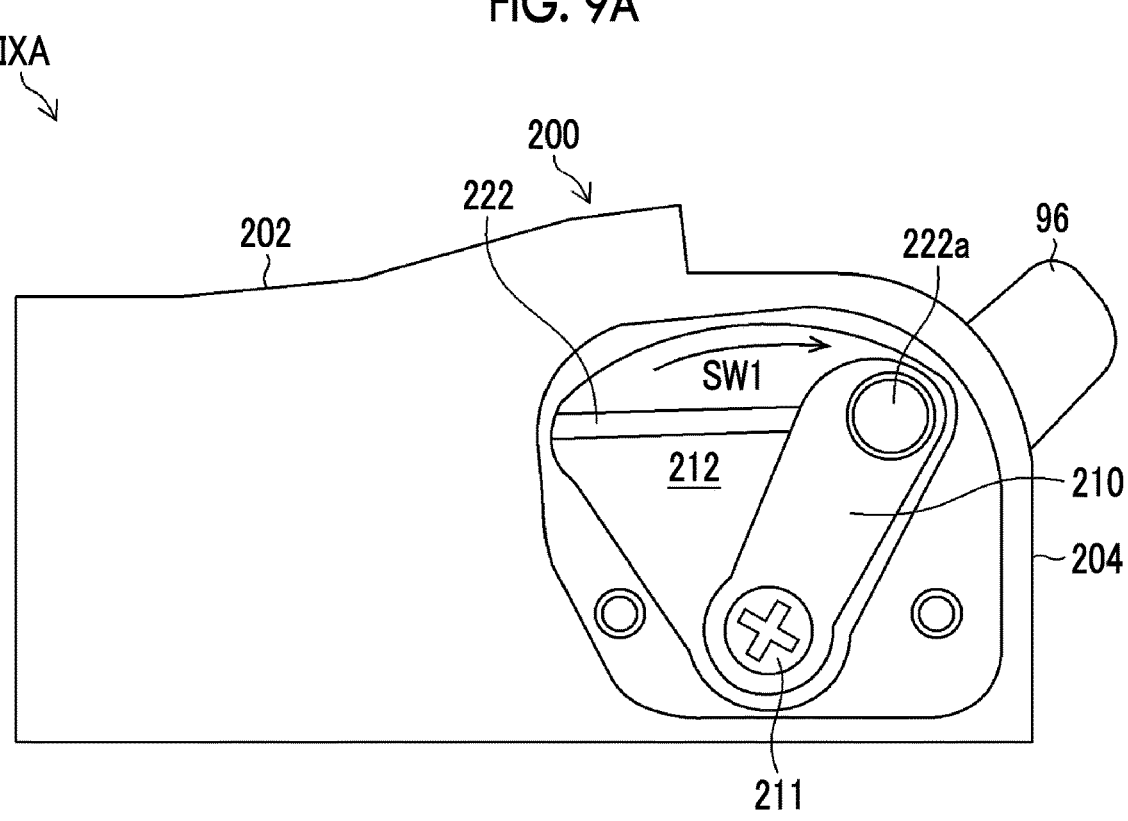
FIGS. 9A and 9B are explanatory views for explaining the rotation of the elevator according to the operation of an operating lever.
Figure 9B:
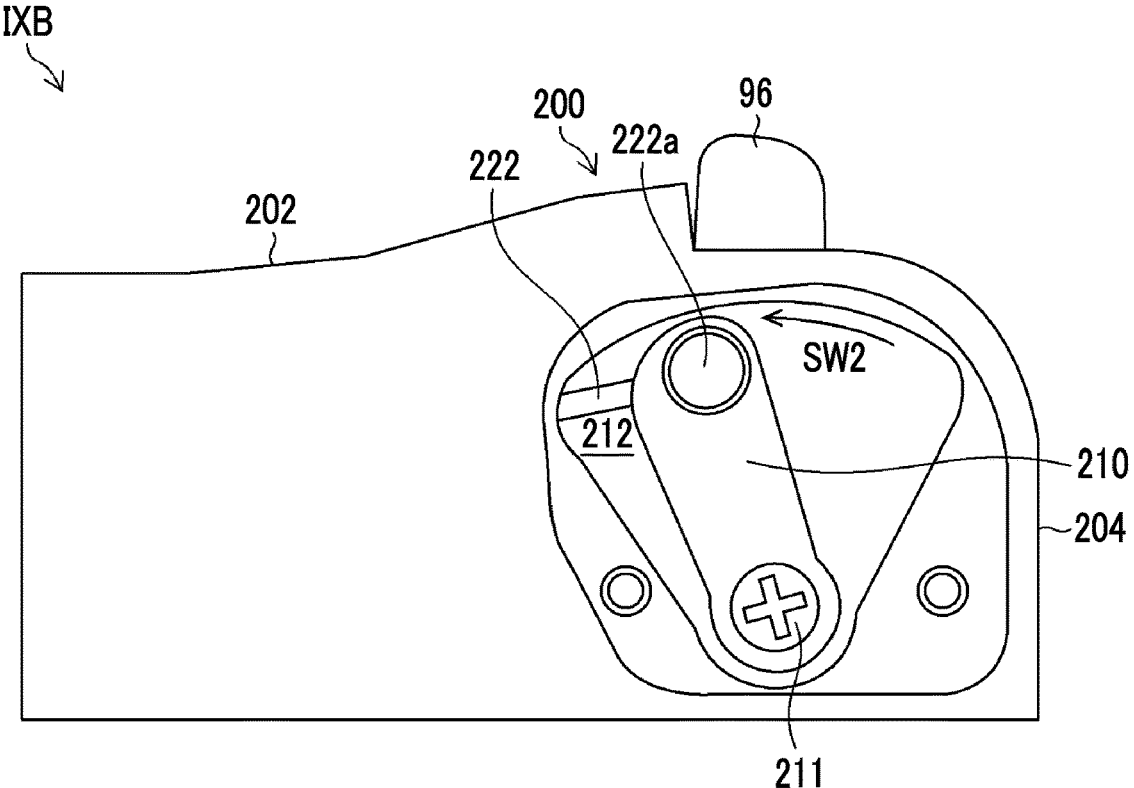

FIGS. 9A and 9B are an explanatory views for explaining the rotation of the elevator 96 according to the operation of the operating lever 43. As indicated by reference numeral IXA in FIG. 9A, in a case where the operating lever 43 is operated to rotate the rotating drum 226A in one direction, the operating wire 222 is pushed, and thereby, the elevator elevating lever 210 moves about the rotation shaft 216 in an SW1 direction. Accordingly, the elevator 96 is rotated in a lodged position along with this rotation.

As indicated by reference numeral IXB in FIG. 9B, in a case where the operating lever 43 is operated to rotate the rotating drum 226A in the opposite direction, the operating wire 222 is pulled, and the elevator elevating lever 210 rotates about the rotation shaft 216 in an SW2 direction opposite to the SW1 direction. Accordingly, the elevator 96 is rotated to an elevated position along with this rotation. In this way, by rotating the rotation shaft 216 via the operating wire 222, the elevator elevating lever 210, and the like through the operation of the operating lever 43, the elevator 96 can be displaced (elevated and lodged).

[First Illumination Window, Second Illumination Window, and Observation Window]

Figure 10:
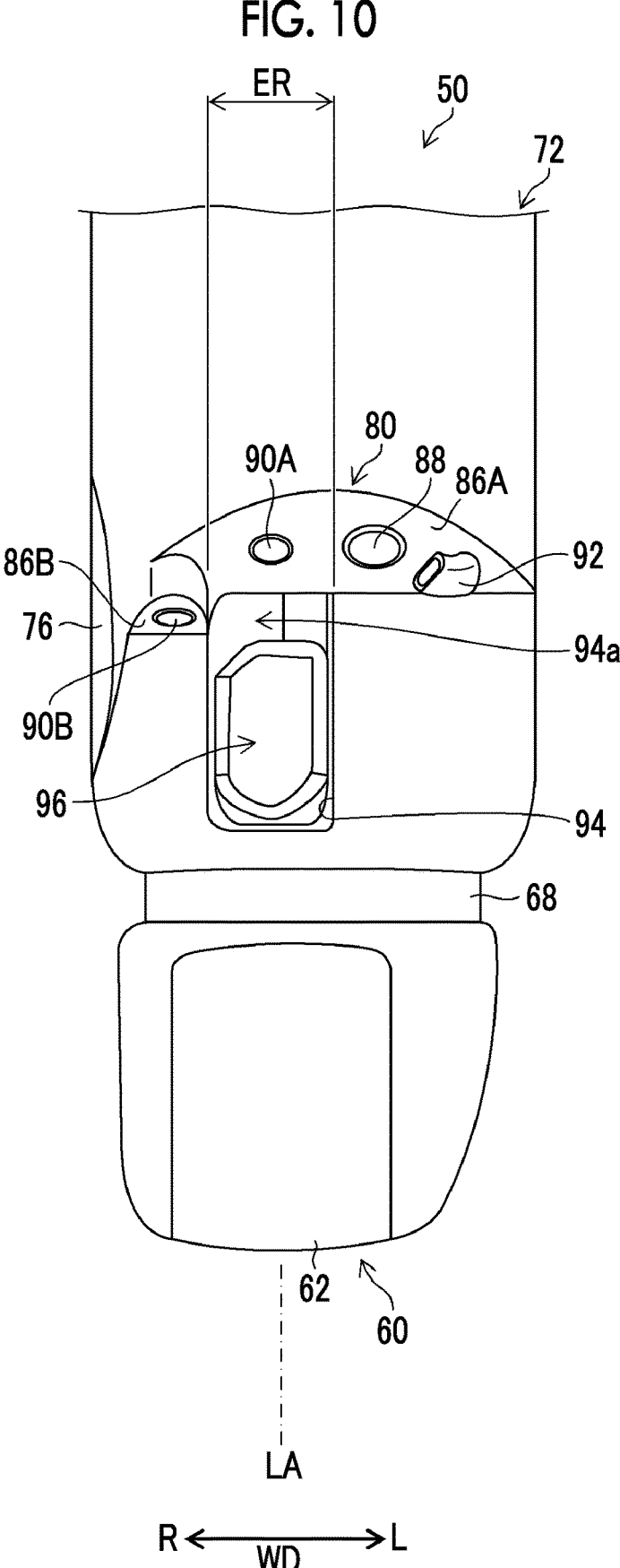
FIG. 10 is a top view of the exterior case.

FIG. 10 is a top view of the exterior case 72. As illustrated in FIG. 10, the first illumination window 90A is formed in a proximal end side region ER in the already-described first inclined surface 86A. The proximal end side region ER is a region on the outer surface of the exterior case 72, which is located at a position shifted from the treatment tool delivery port 94 to the exterior case proximal end side.

More specifically, the proximal end side region ER is a region of the exterior case 72, which is located closer to the exterior case proximal end side than the treatment tool delivery port 94 in the direction along the longitudinal axis LA and is a region within a range where the treatment tool delivery port 94 is formed in the width direction WD. Accordingly, the treatment tool delivered from the treatment tool delivery port 94 and the treatment target region thereof can be illuminated with the illumination light emitted from the first illumination window 90A.

Moreover, in a case where an end part opposite to one end part on the side where the rotation shaft 216 of the elevator 96 is provided is the other end part of the elevator 96, the first illumination window 90A is provided at a position closer to the exterior case proximal end side than the other end part of the elevator 96 in the exterior case 72 (proximal end side region ER) at least in a case where the elevator 96 is in the lodged position. In other words, at least in a case where the elevator 96 is in the lodged position, the other end part of the elevator 96 is located closer to the exterior case distal end side than the first illumination window 90A. Accordingly, the treatment tool delivered from the treatment tool delivery port 94 and the treatment target region thereof can be illuminated with the illumination light emitted from the first illumination window 90A.

In addition, it is more preferable that the first illumination window 90A is provided closer to the exterior case proximal end side than the other end part of the elevator 96 even in a case where the elevator 96 is in the elevated position (that is, regardless of the rotational position of the elevator 96). Accordingly, even in a case where the elevator 96 is rotated (pulled up) to the elevated position, the treatment tool delivered from the treatment tool delivery port 94 and the treatment target region thereof can be illuminated with the illumination light emitted from the first illumination window 90A.

The observation window 88 is provided on the first inclined surface 86A as already described. The observation window 88 is provided at a position closer to the exterior case proximal end side than the treatment tool delivery port 94 in the exterior case 72, similar to the first illumination window 90A, in the direction along the longitudinal axis LA. Accordingly, a treatment tool delivered from the treatment tool delivery port 94 and a treatment target region thereof can be observed through the observation window 88.

Additionally, the observation window 88 is provided at a position on the L direction side with respect to the proximal end side region ER in the first inclined surface 86A. In this way, by disposing the observation window 88 and the first illumination window 90A in the same first inclined surface 86A, that is, at substantially the same position in the direction along the longitudinal axis LA, an observation range 150B of the observation window 88 (refer to FIG. 11) can be illuminated with the illumination light emitted from the first illumination window 90A.

The second illumination window 90B is provided on the second inclined surface 86B of the already-described exterior case 72. Although described in detail below, the second illumination window 90B is different from the first illumination window 90A in the emission direction of the illumination light.

The air and water supply nozzle 92 is provided at a position closer to the L direction side than the observation window 88 in the first inclined surface 86A. As already described, the air and water supply nozzle 92 cleans the observation window 88 by jetting a fluid such as water or air onto the observation window 88. In this case, the formation position of the first illumination window 90A in the proximal end side region ER and the formation position of the second illumination window 90B within the second inclined surface 86B are respectively adjusted such that both the illumination windows 90A and 90B are included in the jetting range of a fluid jetted from the air and water supply nozzle 92. Accordingly, the illumination windows 90A and 90B and the light guide distal end part of each light guide 128 can be cooled by a fluid jetted from the air and water supply nozzle 92.

Figure 11:
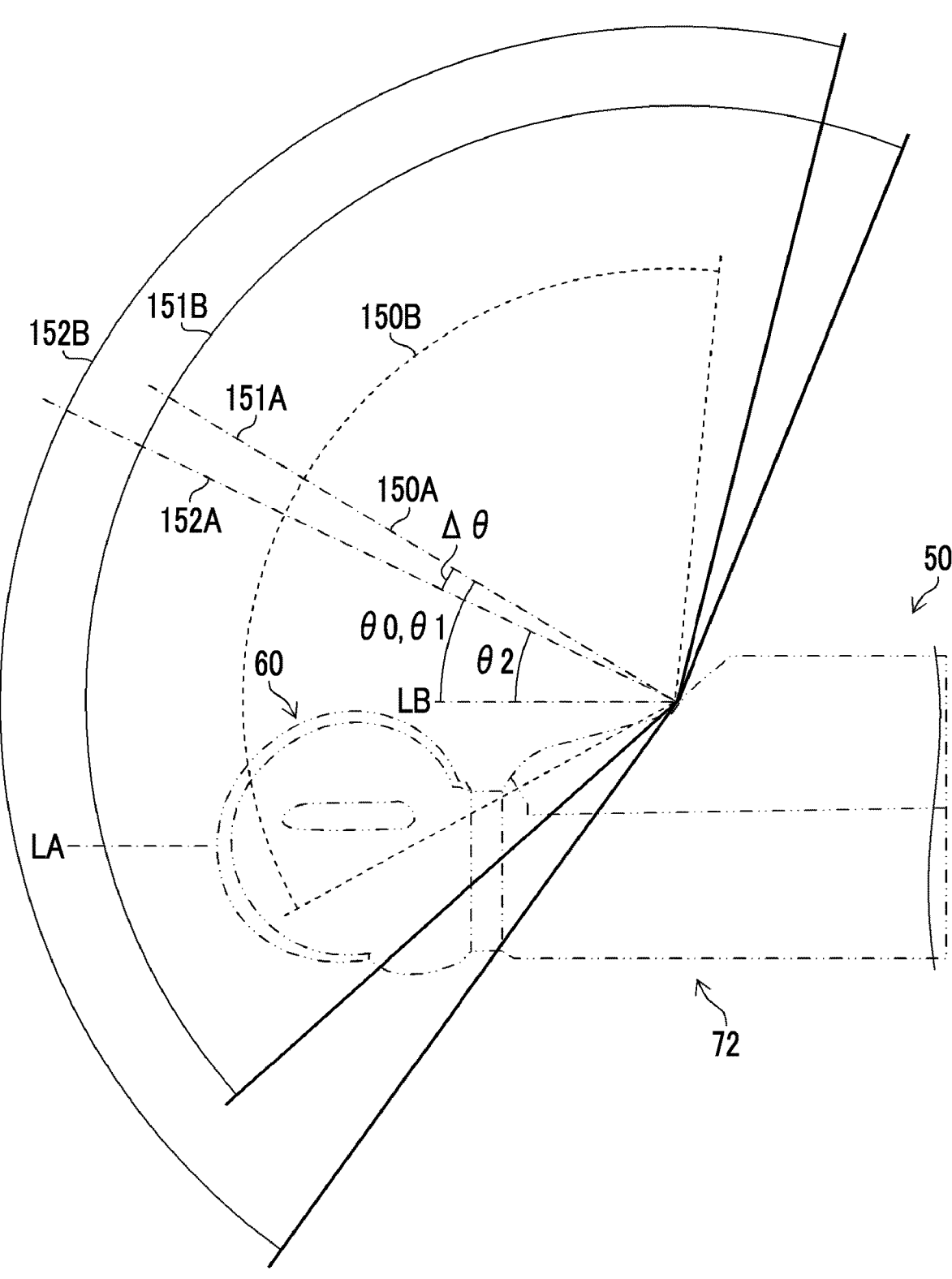
FIG. 11 is an explanatory view for explaining an observation axis and an observation range of the observation window, a first illumination axis and a first illumination range of a first illumination window, and a second illumination axis and a second illumination range of a second illumination window.

FIG. 11 is an explanatory view for explaining an observation axis 150A and an observation range 150B of the observation window 88, a first illumination axis 151A and a first illumination range 151B of the first illumination window 90A, and a second illumination axis 152A and a second illumination range 152B of the second illumination window 90B. In addition, in FIG. 11 (the same applies to FIG. 12 described below), in order to prevent the drawing from becoming complicated, the respective axes and the respective ranges will be described assuming that the observation window 88 and the illumination windows 90A and 90B are at the same position.

As illustrated in FIG. 11, the observation axis 150A is an axis extending from the observation window 88 in a normal direction thereof, the first illumination axis 151A is an axis extending from the first illumination window 90A in the normal direction thereof, and the second illumination axis 152A is an axis extending from the second illumination window 90B in the normal direction thereof. Additionally, each of the observation axis 150A, the first illumination axis 151A, and the second illumination axis 152A is an inclined axis that is inclined toward the exterior case distal end side from the posture perpendicular to both the width direction WD and the longitudinal axis LA. In addition, the observation axis 150A and the first illumination axis 151A are parallel to a normal line of the first inclined surface 86A, and the second illumination axis 152A is parallel to a normal line of the second inclined surface 86B.

An observation axis angle θ0 is the inclination angle of the observation axis 150A with respect to a reference axis LB parallel to the longitudinal axis LA as seen from the width direction WD side (the side perpendicular to the paper surface). A first illumination axis angle θ1 is the inclination angle of the first illumination axis 151A with respect to the reference axis LB as seen from the width direction WD side. A second illumination axis angle θ2 is the inclination angle of the second illumination axis 152A with respect to the reference axis LB as seen from the width direction WD side. In addition, the reference axis LB is an axis that intersects the observation axis 150A in the case of the observation axis angle θ0, an axis that intersects the first illumination axis 151A in the case of the first illumination axis angle θ1, and an axis that intersects the second illumination axis 152A in the case of the second illumination axis angle θ2.

As seen from the width direction WD side, the observation axis angle θ0 and the observation range 150B are respectively set to values such that an angle range from one to the other of the exterior case distal end side of the exterior case 72 [the insertion direction side of the insertion part 20 (the traveling direction side)] and the treatment tool the delivered from the treatment tool delivery port 94 and the treatment target region thereof can be observed through the observation window 88. In addition, it is preferable that the observation axis angle θ0 and the observation range 150B are values that allow observation of the treatment tool delivered from the treatment tool delivery port 94 and the treatment target region thereof in a state where the elevator 96 is rotated to the elevated position.

Since the first illumination axis angle θ1 and the observation axis angle θ0 are equal to each other (including substantially equal), the first illumination axis 151A and the observation axis 150A are parallel to each other (including substantially parallel). Also, the first illumination range 151B includes at least the observation range 150B as seen from the width direction WD side. Accordingly, the first illumination window 90A can illuminate the above-described angle range (observation range 150B) with illumination light.

Since the second illumination axis angle θ2 is smaller than the first illumination axis angle θ1, the second illumination axis 152A is inclined toward the exterior case distal end side with respect to the first illumination axis 151A. In other words, the second inclined surface 86B has an inclination angle closer to an angle perpendicular to the reference axis LB than the first inclined surface 86A.

In a case where the difference between the first illumination axis angle θ1 and the second illumination axis angle θ2 is Δθ, the second illumination range 152B is inclined toward the exterior case distal end side by a difference Δθ with respect to the first illumination range 151B. Therefore, the second illumination range 152B partially overlaps the first illumination range 151B.

In this case, the second illumination axis angle θ2 (difference Δθ) is set to a value such that the observation range 150B is included in at least the second illumination range 152B as seen from the width direction WD side. For this reason, the second illumination window 90B can also be illuminated with the illumination light in the above-described angle range (observation range 150B).

FIG. 12 is a side view of the distal end part 50 of the insertion part 20 inserted into the lumen 154. As illustrated in FIG. 12 and the already-described FIG. 11, by inclining the second illumination window 90B (the second illumination axis 152A and the second illumination range 152B) toward the exterior case distal end side by the difference Δθ with respect to the first illumination window 90A (the first illumination axis 151A and the first illumination range 151B), it is possible to increase the illumination light amount of the illumination light with which the second illumination window 90B illuminates the insertion direction side of the insertion part 20. As a result, for example, in a case where the insertion part 20 is inserted into the narrow lumen 154, the visibility (forward visibility) of an inner wall of the lumen 154 on the insertion direction side of the insertion part 20 is improved.

Moreover, by inclining the second illumination window 90B toward the exterior case distal end side by the difference Δθ with respect to the first illumination window 90A, for example, in a case where an inner wall surface of the narrow lumen 154 such as the duodenum is illuminated, the illumination light amount of the illumination light emitted from the second illumination window 90B to the inner wall surface can be made smaller than the illumination light amount of the illumination light emitted from the first illumination window 90A to the inner wall surface. Accordingly, it is possible to reduce the illumination light amount of the illumination light with which the inner wall surface of the lumen 154 is irradiated, as compared to a case where the second illumination axis angle θ2 has the same size as the first illumination axis angle θ1. As a result, it is possible to prevent the occurrence of halation in the endoscope image due to the excessive illumination light amount of the illumination light on the inner wall surface of the lumen 154. In addition, the illumination only by the second illumination window 90B may be selectively performed as necessary.

Since the first illumination window 90A is disposed in the already-described proximal end side region ER, the treatment tool delivered from the treatment tool delivery port 94 and the treatment target region thereof can be illuminated always from one direction side (the proximal end side region ER side) by the first illumination window 90A. Accordingly, it is possible to prevent the treatment target region from entering the shadow of the elevator 96, the treatment tool, and the like as seen from the first illumination window 90A. Additionally, since the way that the illumination light hits the treatment tool does not change due to the displacement of the treatment tool accompanying the rotation of the elevator 96, the endoscope image is prevented from being not easily seen, and the treatment tool delivered from the treatment tool delivery port 94 and the treatment target region is prevented from coming off the first illumination range 151B. As a result, since it is possible to reliably illuminate the treatment tool delivered from the treatment tool delivery port 94 and the treatment target region thereof with the illumination light emitted from the first illumination window 90A, the visibility of the treatment tool and the treatment target region can be improved.

Moreover, by inclining the first illumination window 90A (the first illumination axis 151A and the first illumination range 151B) toward the exterior case proximal end side by the difference Δθ with respect to the second illumination window 90B (the second illumination axis 152A and the second illumination range 152B), it is possible to increase the illumination light amount of the illumination light with which the first illumination window 90A illuminates the treatment tool delivered from the treatment tool delivery port 94 and the treatment target region thereof. As a result, since the treatment tool and the treatment target region can be reliably illuminated with the illumination light, the visibility of the treatment tool and the treatment target region can be improved.

In this way, by combining the first illumination window 90A with the second illumination window 90B, it is possible to improve the forward visibility of the insertion part 20 and the visibility of the treatment tool and the treatment target region.

[Effects of Present Embodiment]

As described above, in the present embodiment, the first illumination window 90A is disposed in the proximal end side region ER of the exterior case 72. Thus, it is possible to always illuminate the treatment tool delivered from the treatment tool delivery port 94 and the treatment target region thereof from the proximal end side region ER side with the illumination light emitted from the first illumination window 90A. As a result, it is possible to reliably illuminate the treatment tool and the treatment target region thereof with the illumination light regardless of the rotational position of the elevator 96. Accordingly, the visibility of the treatment tool and the treatment target region can be improved.

Additionally, in the present embodiment, the observation window 88 is disposed at the position of the treatment tool delivery port 94 of the exterior case 72 on the exterior case proximal end side. Thus, the treatment tool and the treatment target region can be observed through the observation window 88 regardless of the rotational position of the elevator 96. Accordingly, the visibility of the treatment tool and the treatment target region can be improved.

[Others]

In the above-described embodiment, the entire first illumination window 90A fits within the proximal end side region ER in the width direction WD. However, a portion of the first illumination window 90A may protrude to the L direction side or the R direction side of the proximal end side region ER. However, in order to reliably illuminate the treatment tool and the treatment target region thereof with the illumination light regardless of the rotational position of the elevator 96, the entire first illumination window 90A fits within the proximal end side region ER in the width direction WD, preferably.

In the above embodiment, the first illumination axis angle θ1 of the first illumination axis 151A of the first illumination window 90A is less than 90°. However, the first illumination axis angle θ1 may be 90 (including approximately 90°) depending on the size of the first illumination range 151B of the first illumination window 90A. That is, the proximal end side region ER (the first inclined surface 86A) may be a surface parallel to the longitudinal axis LA.

In the above-described embodiment, the observation window 88 is formed at the position of the proximal end side region ER on the L direction side in the first inclined surface 86A. However, the formation position of the observation window 88 is not particularly limited. However, in order to always observe the treatment tool delivered from the treatment tool delivery port 94 and the treatment target region thereof, it is preferable that the observation window 88 is provided at a position closer to the exterior case proximal end side than the treatment tool delivery port 94 in the exterior case 72.

In the above embodiment, the second illumination window 90B is formed on the second inclined surface 86B. However, the formation position of the second illumination window 90B is not particularly limited. Additionally, in the above embodiment, the second illumination axis angle θ2 is smaller than the first illumination axis angle θ1. However, the second illumination axis angle θ2 may be larger than the first illumination axis angle θ1 or both may be equal to each other. Moreover, in the above-described embodiment, the second illumination window 90B is provided at a position closer to the exterior case distal end side than the proximal end side region ER in the exterior case 72 but may be provided at a position closer to the exterior case proximal end side than the treatment tool delivery port 94. Moreover, the second illumination window 90B may be omitted as long as the already-described forward visibility and the visibility of the treatment tool and the treatment target region can be ensured only with the first illumination window 90A.

In the above embodiment, the observation axis 150A and the first illumination axis 151A are parallel to each other but both may not be parallel to each other. For example, the observation axis angle θ0 may be an angle between the first illumination axis angle θ1 and the second illumination axis angle θ2.

In the above-described embodiment, an example in which the elevator 96 is rotated via the operating wire 222 and the elevator elevating lever 210 has been described. However, the method of rotating the elevator 96 is not particularly limited, and a publicly known method can be adopted.

In the above embodiment, the first inclined surface 86A is parallel to the observation window 88 and the first illumination window 90A. However, the observation window 88 and the first illumination window 90A may be provided not to be parallel to the first inclined surface 86A. Additionally, similarly, the second illumination window 90B may be provided not to be parallel to the second inclined surface 86B.

In the above embodiment, the ultrasound endoscope 10 including the ultrasound observation part 60 (ultrasound transducer 62) has been described as an example. However, the present invention can also be applied to an endoscope including the elevator 96 that guides the treatment tool, for example other side-view endoscopes such as a duodenoscope.

EXPLANATION OF REFERENCES

2: ultrasound examination system
10: ultrasound endoscope
12: ultrasound processor device
14: endoscope processor device
16: light source device
18: monitor
20: insertion part
22: operating part
24: universal cord
27: ultrasound connector
28: endoscope connector
30: light source connector
32: tube
34: tube
36: air and water supply button
38: suction button
42: angle knob 43: operating lever
44: treatment tool insertion port
50: distal end part
52: bending part
54: flexible part
60: ultrasound observation part
62: ultrasound transducer
64: balloon
66: locking ring
68: locking groove
70: supply and discharge port
71: opening part
72: exterior case
72a: exterior case body
72b: exterior case lid
73: partition wall
74: groove part
75: fitting hole
76: lever housing lid
77: bolt
80: endoscope observation part
86A: first inclined surface
86B: second inclined surface
88: observation window
90A: first illumination window
90B: second illumination window
92: air and water supply nozzle
94: treatment tool delivery port
94a: elevator housing chamber
96: elevator
96a: guide surface
100: treatment tool insertion channel
102: air and water supply pipe line
104: balloon pipe line
106: suction pipeline
108: air supply pipe line
110: water supply pipe line
112: balloon water supply pipe line
114: balloon drainage pipe line
116: air supply source pipe line
118: water supply tank
120: water supply source pipe line
122: branch pipe line
124: suction pump
126: suction source pipe line
128: light guide
129: air supply pump
150A: observation axis
150B: observation range
151A: first illumination axis
151B: first illumination range
152A: second illumination axis
152B: second illumination range
154: lumen
200: elevating case
202: base
202a: through hole
203A: light guide holding groove
203B: light guide holding groove
204: partition wall
206: side wall surface
208: facing wall surface
208a: cutout part
210: elevator elevating lever
211: bolt
212: lever housing chamber
214: holding hole 216: rotation shaft
220: bolt hole
222: operating wire
222a: distal end side coupling part
222b: proximal end side coupling part
224: wire insertion hole
226: elevator operating mechanism
226A: rotating drum
226B: crank member
226C: slider
ER: proximal end side region
LA: longitudinal axis
LB: reference axis
NV: normal direction
WD: width direction
$\Delta\theta$: difference
$\theta0$: observation axis angle
$\theta1$: first illumination axis angle
$\theta2$: second illumination axis angle
What is claimed is:

1. An endoscope comprising:
a distal end part body that is provided on a distal end side of an insertion part and has a distal end, a proximal end, and a longitudinal axis;
a treatment tool delivery port that is formed in the distal end part body and delivers a treatment tool inserted into the insertion part;
an elevator that is rotatably supported in the treatment tool delivery port of the distal end part body and controls a delivery direction of the treatment tool delivered from the treatment tool delivery port; and
a first illumination window that is provided on the distal end part body, the first illumination window is configured to emit illumination light,
a second illumination window provided at a position on an other direction side opposite to a one direction side in the width direction with respect to the proximal end side region in the distal end part body,
an observation window that is provided at a position closer to a proximal end side of the distal end part body than the treatment tool delivery port in the distal end part body,
wherein the first illumination window is provided in a proximal end side region at a position shifted from the treatment tool delivery port to the proximal end side of the distal end part body in the distal end part body,
wherein the first illumination window is disposed closer to the proximal end of the distal end part body than both the treatment tool delivery port and the elevator,
wherein in a case where a direction perpendicular to both the longitudinal axis and a normal direction of an opening surface of the treatment tool delivery port is a width direction of the treatment tool delivery port, the proximal end side region in which the first illumination window is disposed is a region in the distal end part body, which is located closer to the proximal end side of the distal end part body than the treatment tool delivery port and is present within a range in which the treatment tool delivery port is formed in the width direction,
wherein a first illumination range of illumination light emitted from the first illumination window includes an observation range of the observation window,
wherein in a case where a direction perpendicular to both the longitudinal axis and a normal direction of an opening surface of the treatment tool delivery port is a width direction of the treatment tool delivery port, the observation window is provided at a position on one direction side in the width direction with respect to the proximal end side region in the distal end part body, wherein the second illumination window illuminates a second illumination range that partially overlaps the first illumination range and includes the observation range.

2. The endoscope according to claim 1, further comprising:

an elevator support member that is coupled to one end part of the elevator and rotatably supports the elevator between an elevated position and a lodged position, wherein the other end part of the elevator opposite to the one end part is provided at a position closer to a distal end side of the distal end part body than the first illumination window at least in a case where the elevator is at the lodged position.

3. The endoscope according to claim 1, wherein in a case where a direction perpendicular to both the longitudinal axis and a normal direction of an opening surface of the treatment tool delivery port is a width direction of the treatment tool delivery port, a first illumination axis of the first illumination window is inclined toward a distal end side of the distal end part body from a posture perpendicular to both the width direction and the longitudinal axis, and the proximal end side region in which the first illumination window is disposed is an inclined surface having the first illumination axis as a normal line.

4. The endoscope according to claim 1, wherein both a first illumination axis of the first illumination window and a second illumination axis of the second illumination window are inclined toward a distal end side of the distal end part body from a posture perpendicular to both the width direction and the longitudinal axis, and a second illumination axis angle is smaller than a first illumination axis angle in a case where an inclination angle of the first illumination axis with respect to a reference axis parallel to the longitudinal axis as seen from the width direction side is the first illumination axis angle and an inclination angle of the second illumination axis with respect to the reference axis as seen from the width direction side is the second illumination axis angle.

5. The endoscope according to claim 4, wherein an observation axis of the observation window is inclined toward the distal end side of the distal end part body from the posture perpendicular to both the width direction and the longitudinal axis, and an observation axis angle is equal to the first illumination axis angle in a case where an inclination angle of the observation axis with respect to the reference axis as seen from the width direction side is the observation axis angle.

6. The endoscope according to claim 1, further comprising:

an ultrasound transducer that is provided in the distal end part body and is located closer to a distal end side of the distal end part body than the treatment tool delivery port.

7. The endoscope according to claim 1, wherein the first illumination window is disposed on a first inclined surface, the second illumination window is disposed on a second inclined surface, and an inclination angle of the first inclined surface and an inclination angle of the second inclined surface are different from each other.

\* \* \* \* \*